United States Patent [19]
Berger et al.

[11] Patent Number: 5,458,881
[45] Date of Patent: Oct. 17, 1995

[54] N-ACYLATED DERIVATIVES OF MIXTURES OF AMINO ACIDS DERIVED FROM HYDROLYSATES OF CEREAL PROTEINS AND THEIR APPLICATIONS

[75] Inventors: Christian Berger, Ecully; Paul Gacon, Tassin la Demi-Lune, both of France

[73] Assignee: Givaudan-Lavirotte, Ecully, France

[21] Appl. No.: 150,032

[22] PCT Filed: Jun. 3, 1992

[86] PCT No.: PCT/FR92/00489

§ 371 Date: Nov. 16, 1993

§ 102(e) Date: Nov. 16, 1993

[87] PCT Pub. No.: WO92/21318

PCT Pub. Date: Oct. 12, 1992

[30] Foreign Application Priority Data

Jun. 3, 1991 [FR] France ................... 91 06672

[51] Int. Cl.[6] ................ A61K 6/00; A61K 7/00
[52] U.S. Cl. ................ 424/401; 554/61; 554/63; 562/516

[58] Field of Search ............ 554/63, 61; 562/516; 424/401

[56] References Cited

U.S. PATENT DOCUMENTS

| | | | |
|---|---|---|---|
| 3,927,047 | 12/1975 | Ichikawa et al. | 260/404 |
| 3,985,722 | 10/1976 | Yoshida et al. | 260/112 |
| 4,828,824 | 5/1989 | Grollier | 424/52 |

FOREIGN PATENT DOCUMENTS

| | | |
|---|---|---|
| 0308278 | 3/1989 | European Pat. Off. . |
| 2603800 | 3/1988 | France . |
| 3422496 | 12/1985 | Germany . |
| 61-137808 | 6/1986 | Japan . |
| 1153408 | 5/1969 | United Kingdom . |
| 2095994 | 10/1982 | United Kingdom . |

*Primary Examiner*—José G. Dees
*Assistant Examiner*—Deborah D. Carr
*Attorney, Agent, or Firm*—Oliff & Berridge

[57] ABSTRACT

N-acylated derivatives of amino acid mixtures from cereal protein hydrolysates as well as their salts are useful in cosmetic and detergent compositions.

13 Claims, No Drawings

N-ACYLATED DERIVATIVES OF MIXTURES OF AMINO ACIDS DERIVED FROM HYDROLYSATES OF CEREAL PROTEINS AND THEIR APPLICATIONS

TECHNICAL FIELD

The present invention relates to new N-acylated derivatives from mixtures of amino acids derived by total hydrolysis of proteins of plant origin and their salts, as well as their application to the field of cosmetics and detergents.

BACKGROUND

At the present time, N-acylated derivatives of mixtures of amino acids obtained by hydrolysis of proteins of animal origin are currently employed for cosmetic purposes.

Because of the their amphiphilic structure, these polyacylated lipoamino acids can progress rapidly through the first cell layers either to restore deficient structures or to release their active ingredients within the epidermis.

Hence these lipoamino acid structures are particularly useful biological vectors as skin physiology regulators and prove to be appropriate for multiple applications, particularly in cosmetics.

The sources of these amino acid mixtures are today essentially collagen, elastin, keratin, and casein.

In view of their animal origin, these hydrolysates unfortunately have potential risks of contamination by pathogens which it would be desirable to avoid; users tend with increasing frequency to avoid animal-derived compounds for any application intended for human beings.

Moreover, British Patent No. 1,153,408 describes N-acylated derivatives of mixtures of amino acids obtained by hydrolysis of proteins of plant origin. However, the precise nature of these proteins is not described. Moreover, the present inventors have been able to ascertain that depending on the nature of the plant from which the protein is derived, the resulting compounds can have very different properties. They thus observed that N-acylated derivatives of mixtures of amino acids from hydrolysates of leguminous proteins such as soy had certain disadvantages.

Thus, solutions of such N-acylated derivatives, particularly solutions of salts of these derivatives, have relatively substantial coloration, which is troublesome in certain applications, particularly in the field of cosmetics. Moreover it is often necessary to locate the pH of cosmetic compositions at approximately 5.5, namely at a pH approximately that of the skin, to decrease their aggressiveness to the skin. Now the inventors have ascertained that solutions containing such N-acylated derivatives of leguminous proteins such as soy become cloudy as soon as their pH drops lower than approximately 6.8. Yet one important and frequently sought-after characteristic of cosmetic compositions is their clarity.

Moreover, said derivatives derived in particular from soy proteins have a relatively high ability to increase viscosity in an aqueous solution, which sometimes makes it difficult to prepare certain compositions, particularly cosmetic compositions, with the aid of such solutions.

SUMMARY OF THE INVENTION

Thus the present invention has as an object novel N-acylated derivatives of mixtures of amino acids derived from plant proteins, which allow very low-color solutions that are stable even at a pH of approximately 5.5 and have a relatively low ability to increase viscosity in an aqueous solution to be obtained.

Another object of the invention is cosmetic compositions containing said derivatives, which compositions have a cosmetic activity comparable or even superior to compositions containing N-acylated derivatives of mixtures of amino acids derived from animal protein hydrolysates.

A third object of the present invention is detergent compositions containing said N-acylated derivatives.

Hence the invention comprises new N-acylated derivatives of mixtures of amino acids with general formula I:

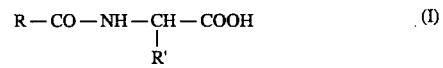

wherein

R represents a saturated or unsaturated, linear or branched radical with $C_4$ to $C_{30}$, and R' represents an amino acid main chain, as well as the salts of these derivatives of amino acid mixtures, which amino acid mixtures are derived from cereal protein hydrolysates.

DETAILED DESCRIPTION OF EMBODIMENTS OF THE INVENTION

According to one advantageous feature of the present invention, R represents a radical with $C_7$ to $C_{19}$, and more particularly R represents a radical with $C_7$, $C_{11}$, or $C_{15}$ such that the R—CO residue in formula I represents a capriloyl, lauroyl, or palmitoyl radical.

The proteins from which the amino acid mixtures are derived may come from various cereal species such as corn, barley, or, preferably, wheat.

As an example, the average amino acid composition of wheat proteins is the following:

| Alanine | 3.9 | Lysine | 2.0 |
|---|---|---|---|
| Arginine | 5.0 | Methionine | 2.0 |
| Aspartic acid | 5.3 | Phenylalanine | 5.3 |
| Cystine | 2.7 | Proline | 4.9 |
| Glutamic acid | 35.2 | Serine | 5.4 |
| Glycine | 3.5 | Threonine | 3.4 |
| Histidine | 2.0 | Tryptophan | 1.0 |
| Isoleucine | 4.1 | Tyrosine | 3.6 |
| Leucine | 8.4 | Valine | 5.1 |

When they are in the form of salts, the N-acylated derivatives of the invention can in particular be metal salts or salts of organic bases. Thus the acid function of these substances can be salified by cations of alkaline metals such as sodium or potassium or alkaline-earth metals such as calcium or magnesium or other metals such as cobalt, iron, aluminum, manganese, copper, zinc, or by organic bases such as arginine, lysine, mono-, di-, or triethanolamine, ornithine, histidine, morpholine, or choline. Said acid function can also be salified by ammonia.

When they are salified by the aluminum cation, the N-acylated derivatives of the invention can be in the form of monobasic or dibasic aluminum salts.

These N-acylated derivatives of amino acids obtained by hydrolysis of cereal proteins can be obtained, in a manner known per se, in two stages.

The first stage comprises total hydrolysis of the cereal protein by heating said cereal protein placed in an acid aqueous medium, at temperatures of between 60° and 130° C.

Acidification of said medium can be accomplished by strong acids such as sulfuric acid or hydrochloric acid.

The second stage comprises acylation of the hydrolysate previously obtained with the aid of carboxylic activated derivatives of the formula RCOOH, R being defined as above.

Such derivatives are for example the symmetric anhydrides of these acids, or acid chlorides. The operation is generally conducted at a temperature between 0° C. and 100° C.

The N-acylated derivatives obtained can be purified by methods such as crystallization or chromatography.

The invention also extends to salts of N-acylated derivatives of amino acids obtained by total hydrolysis of cereal proteins. These salts can be prepared by reacting said N-acylated derivatives with organic or inorganic bases or with metal derivatives.

Organic or inorganic bases that may enter into the framework of the present invention and can be cited are potassium hydroxide, sodium hydroxide, lime, magnesia, ammonia, triethanolamine, diethanolamine, monoethanolamine, morpholine, lysine, histidine, arginine, ornithine and choline.

The salts obtained by reaction with metal derivatives that may be cited are the salts of zinc, aluminum, copper, cobalt, iron and manganese.

The present invention also relates to cosmetic compositions containing at least one N-acylated derivative of amino acids obtained by total hydrolysis of cereal proteins or a salt of said derivatives, as described above.

Cosmetic compositions that may be cited are creams, milks, foams, aerosols, gels, sticks, oils, emulsions, shampoos, soaps, toothpastes, and aqueous or water-alcohol lotions.

In said cosmetic compositions, the aforementioned N-acylated derivatives and/or the salts of these derivatives are present in proportions of 0.1 to 50% and preferably 0.5 to 20 wt. % relative to the total weight of the composition. In these cosmetic compositions, the N-acylated derivatives of the invention can in particular be useful as emollients or regulators of skin pH.

The invention also relates to detergent compositions containing at least one N-acylated derivative of amino acids and/or a salt of these derivatives, as defined above. Said derivatives and/or their salts are present in proportions of 0.1 to 50 wt. %, and more generally 10 to 30 wt. % relative to the total weight of the composition.

In the framework of the present invention, "detergent composition" is understood to be a composition for other than cosmetic use. Such detergent compositions can in particular be compositions for washing textiles and dishes or compositions for cleaning and maintaining surfaces, particularly floors.

These detergent compositions according to the invention can in particular be suited for washing delicate fabrics, for example wool, silk, cotton, or linen.

The following examples are intended to illustrate the present invention:

EXAMPLE 1

Preparation of the Sodium Salt of the N-Lauroyl Derivative of Amino Acids obtained By Total Hydrolysis of Wheat Protein A mixture composed of 357 g of wheat protein, 225 cc of water, and 450 cc of 30% weight/weight hydrochloric acid is refluxed for 8 hours. After cooling, 225 cc of water are added to the reaction mixture, which is then adjusted to a pH of 3.5 with 380 cc of 30% weight/weight sodium hydroxide. A decolorizing charcoal (20 g) is then added and left in contact for one hour under agitation, then the suspension is filtered.

The aqueous solution is then raised to pH 10.5 with the aid of 310 cc of 30% weight/weight sodium hydroxide, then heated to 40°–45° C. under vacuum ($8 \times 10^2$ Pa) for 4 hours; the reaction mixture is then adjusted to pH 3.5 with 150 cc of 30% weight/weight hydrochloric acid and treated with 20 g of decolorizing charcoal for 20 minutes under agitation. After filtration, 2285 g of wheat protein hydrolysate are obtained.

Water (150 cc) is added to 500 g of this hydrolysate, the temperature is raised to 30° C., then the pH is adjusted to 10.5 with 60 cc of 30% weight/weight sodium hydroxide; then, under agitation, 71.5% lauroyl chloride and 40 cc of 30% weight/weight sodium hydroxide are poured in simultaneously, holding the pH at 10.5±0.3 and the temperature below 40° C. for approximately 1 hour. After the end of the addition, the temperature is held at 40° C. for 30 minutes then at 60° C. for 1 hour. The temperature is then raised to 80° C.; then 115 cc of 30% weight/weight hydrochloric acid are added to lower the pH to 1. Agitation is then stopped and the lower aqueous phase is drawn off. Under agitation, 300 g of water are added to the organic phase under agitation and the mixture is raised to pH 7 with 25 cc of 30% weight/weight sodium hydroxide. The solution is treated at 70° C. with 10 g of decolorizing charcoal, then filtered, yielding 450 g of a 30% aqueous solution of the sodium salt of the N-lauroyl derivative of amino acids obtained by total hydrolysis of the wheat protein in the form of a clear viscous yellow to amber-yellow solution.

EXAMPLE 2

For comparison, a 22% solution of a sodium salt of the N-lauroyl derivative of amino acids obtained by total hydrolysis of soy protein is prepared, proceeding as in Example 1 but substituting a soy protein for the wheat protein.

Measuring the coloration of this solution at 22%, obtained from soy proteins, shows a coloration of 30 Hazen, while the solution in Example 1, with 30% active material, obtained from a wheat protein, shows a coloration of only 20 Hazen.

Moreover, the viscosity of these two solutions, measured by capillarity, is 260 mPa/sec; a solution of 30 wt. % of active material according to the invention thus allows a viscosity identical to that obtained with a 22 wt. % solution of an active material derived from a soy protein to be obtained.

Thus it is shown that the compounds of the invention lead to low viscosity.

Finally, the solution obtained from a wheat protein remains clear up to pH values of approximately 5.6. On the other hand, the solution obtained from a soy protein becomes cloudy as soon as the pH drops below the value of approximately 6.8.

EXAMPLES 3 TO 7

These examples relate to cosmetic compositions according to the invention.

EXAMPLE 3

Anti-Acne Cream Formula

|     |     |                                                                      |       |
| --- | --- | -------------------------------------------------------------------- | ----- |
|     |     | Polyoxyethylenated glycolized saturated $C_{10}$ to $C_{18}$ glycerides | 5     |
|     |     | Glycerol monostearate                                                | 3     |
|     | I   | Polyoxpropylene (2) myristyl ether propionate                        | 3     |
| III |     | Polydimethylsiloxane                                                 | 2     |
|     |     | Cholecithin                                                          | 2     |
|     |     | Mono-, dipalmitostearate of polyethylene glycol                      | 12    |
|     | II  | Sweet almond oil                                                     | 2     |
|     |     | Capryloyl derivative of wheat protein amino acids                    | 2     |
|     |     | Preservative                                                         | 0.08  |
|     | IV  | Glycerin                                                             | 2     |
|     |     | Demineralized water                                                  | 61.62 |
|     |     | 30% NaOH                                                             | 0.8   |
|     |     | Extract of bitter orange peel (concentrate for syrup)                | 0.5   |
|     | V   | Collagen-glycosaminoglycane complex                                  | 2     |
|     |     | Demineralized water                                                  | 2     |

Method

Cholecithin is dissolved in the phase I ingredients and the solution is cooled to 75° C. The other ingredients of the oily phase (II) are added. Phases III and IV are heated separately at 75° C. and IV is poured into III; the mixture is neutralized with 30% NaOH then cooled to 30° C. Phase V is then added.

EXAMPLE 4

Anti-Irritant and Soothing Cream Formula

|     |                                                   |      |
| --- | ------------------------------------------------- | ---- |
|     | Glycol mono-, distearate and polyoxyethylene stearate | 7    |
|     | Palmitoyl derivative of wheat protein amino acids | 4    |
| I   | Kernel oil                                        | 5    |
|     | Isostearyl isostearate                            | 3    |
|     | Polydimethylsiloxane                              | 3    |
|     | Vaseline oil                                      | 2    |
|     | Demineralized water                               | 71.9 |
| II  | Preservative                                      | 0.3  |
|     | Glycerin                                          | 2    |
|     | Grindelia fluid extract                           | 0.5  |
|     | Hyaluronic acid                                   | 1    |
|     | α-bisabolol                                       | 0.2  |
|     | Fragrance                                         | 0.1  |

Phases I and II are heated separately at 75° C. Phase II is then poured into I and the mixture emulsified in a centrifuge for 5 minutes. The mixture is left to cool slowly and the three remaining active principles are incorporated thereinto at 40° C.

EXAMPLE 5

Normal Protection Cream Formula

|     |                                                   |       |
| --- | ------------------------------------------------- | ----- |
|     | 1,2-propylene glycol mono-, distearate            | 7     |
|     | Palmitoyl derivative of wheat protein amino acids | 2     |
| I   | Avocado oil                                       | 1     |
|     | sweet almond oil                                  | 2     |
|     | Beeswax                                           | 0.5   |
|     | 2-octyldodecyl myristate                          | 2     |
|     | UVB sunscreen                                     | 1     |
|     | Demineralized water                               | 83.32 |
| II  | Xanthan gum                                       | 0.3   |
|     | Preservative                                      | 0.08  |
|     | 30% NaOH                                          | 0.1   |
|     | Vitamin E acetate                                 | 0.5   |
|     | Fragrance                                         | 0.2   |

An aqueous dispersion of xanthan gum is prepared. This dispersion is heated in the presence of a preservative at 75° C., as is Phase I. Phase II is then poured into Phase I and the mixture thus obtained is treated with 30% sodium hydroxide. This is cooled to 30° C. before incorporating the vitamin E acetate and fragrance.

EXAMPLE 6

Baby Shampoo Formula

|     |                                                                          |      |
| --- | ------------------------------------------------------------------------ | ---- |
|     | Sodium lauryl ether sulfate                                              | 12   |
|     | Lauroyl derivative of wheat protein amino acids, sodium salt (30% aqueous solution) | 20   |
| A   | Polyethylene glycol 200 glyceryl stearate                                | 10   |
|     | Polyethylene glycol 6000 distearate                                      | 0.5  |
|     | Sodium propyl parahydroxybenzoate                                        | 0.15 |
|     | Demineralized water qs 100 g                                             |      |
|     | Ethoxyl sorbitan monolaurate                                             | 3    |
| B   |                                                                          |      |
|     | Fragrance                                                                | 0.15 |
| C   | 1% water-soluble dye solution                                            | 0.1  |

Method

Phase A is heated to 70° C. and held at this temperature under agitation for 20 minutes. It is then cooled to 30° C. so that B, precooled to 30° C. can be added to it C is added to the mixture of A and B.

EXAMPLE 7

Normal Hair Shampoo Formula

|     |                                                                          |       |
| --- | ------------------------------------------------------------------------ | ----- |
|     | Sodium lauryl ether sulfate                                              | 25    |
|     | Disodium nonoxynoll-10-sulfosuccinate                                    | 10    |
|     | Lauroyl derivative of wheat protein amino acids, sodium salt (30% aqueous solution) | 10    |
| A   | NaCl                                                                     | 3     |
|     | Polyethylene glycol 6000 distearate                                      | 1     |
|     | Sodium methyl parahydroxybenzoate                                        | 0.18  |
|     | Sodium propyl parahydroxybenzoate                                        | 0.04  |
|     | Water                                                                    | 47.13 |
|     | Ethoxyl sorbitan monolaurate                                             | 1.5   |

| | -continued | |
|---|---|---|
| B | | |
| | Fragrance | 0.15 |
| C | Camomile glycol extract | 2 |

This shampoo is made by a method identical to that described in Example 6.

What is claimed is:

1. N-acylated derivatives of mixtures of amino acids of the formula I:

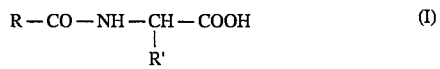

wherein:
R represents a saturated or unsaturated linear or branched $C_4$ to $C_{30}$ radical,
R' represents an amino acid main chain, and salts of these derivatives, said mixtures of amino acids being derived from cereal protein hydrolysates.

2. N-acylated derivatives according to claim 1, characterized by R representing a $C_7$ to $C_{19}$ radical.

3. N-acylated derivatives according to claim 1 R representing a $C_7$, $C_{11}$, or $C_{15}$ radical, so that the R—CO residue in said formula I represents a capriloyl, lauroyl, or palmitoyl radical.

4. N-acylated derivatives according to claim 1 said salts being metal salts or organic-base salts.

5. N-acylated derivatives according to claim 4, said metal salts being alkali metal salts or alkaline-earth metal salts.

6. N-acylated derivatives according to claim 1 said protein being a wheat protein.

7. N-acylated derivatives according to claim 5, said metal salts being sodium or potassium salts.

8. N-acylated derivatives according to claim 5, said alkaline-earth metal salts being calcium or magnesium salts.

9. Cosmetic composition containing (a) at least one member selected from the group consisting of (i) N-acylated derivatives of mixtures of amino acids of the formula I recited in claim 1 and (ii) salts of said N-acylated derivatives, and a cosmetically acceptable carrier.

10. Cosmetic composition according to claim 9, containing an amount of 0.1 to 50 wt. % of said at least one member relative to the total weight of the composition.

11. Cosmetic composition according to claim 10, said amount of said at least one member being 0.1 to 20 wt. %.

12. A cosmetic method, comprising applying to skin a cosmetically effective amount of at least one member selected from the group consisting of (i) N-acylated derivatives of mixtures of amino acids of the formula I recited in claim 1 and (ii) salts of said N-acylated derivatives.

13. Cosmetic composition according to claim 9, said composition being in a form selected from the group consisting of creams, milks, foams, aerosols, gels, sticks, oils, emulsions, soaps, shampoos, toothpastes, aqueous lotions and alcohol lotions.

* * * * *